(12) United States Patent
Juan

(10) Patent No.: US 7,428,433 B2
(45) Date of Patent: Sep. 23, 2008

(54) HEART RATE MONITOR ASSEMBLY

(76) Inventor: Cheng-Pin Juan, No. 16-3, Lane 852, Tu Cheng Road, Ta Li City, Taichung Hsien (TW)

( * ) Notice: Subject to any disclaimer, the term of this patent is extended or adjusted under 35 U.S.C. 154(b) by 449 days.

(21) Appl. No.: 11/208,711

(22) Filed: Aug. 23, 2005

(65) Prior Publication Data

US 2007/0055120 A1    Mar. 8, 2007

(51) Int. Cl.
*A61B 5/0408* (2006.01)
(52) U.S. Cl. .................................................. 600/390
(58) Field of Classification Search ................ 600/390
See application file for complete search history.

(56) References Cited

U.S. PATENT DOCUMENTS

| | | | | |
|---|---|---|---|---|
| 4,129,125 A | * | 12/1978 | Lester et al. ................ | 600/484 |
| 5,491,474 A | * | 2/1996 | Suni et al. ............... | 340/870.31 |
| 5,778,880 A | * | 7/1998 | Chen .......................... | 600/509 |
| 6,272,365 B1 | * | 8/2001 | Ronkainen et al. .......... | 600/390 |
| 2005/0096556 A1 | * | 5/2005 | Hsieh Chen ................ | 600/509 |
| 2006/0058695 A1 | * | 3/2006 | Chen .......................... | 600/509 |

* cited by examiner

*Primary Examiner*—Lee S Cohen

(57) ABSTRACT

A heart rate monitor assembly includes a data processing unit which includes a case in which a data processor and a power supply device are received. The case includes two L-shaped holes and two conductive plates are received in the case and located in the two L-shaped holes and connected to the data processor. A belt has two connection ends and each connection end has an L-shaped connector which is removably engaged with the L-shaped hole corresponding thereto and connected to the two conductive plate.

5 Claims, 3 Drawing Sheets

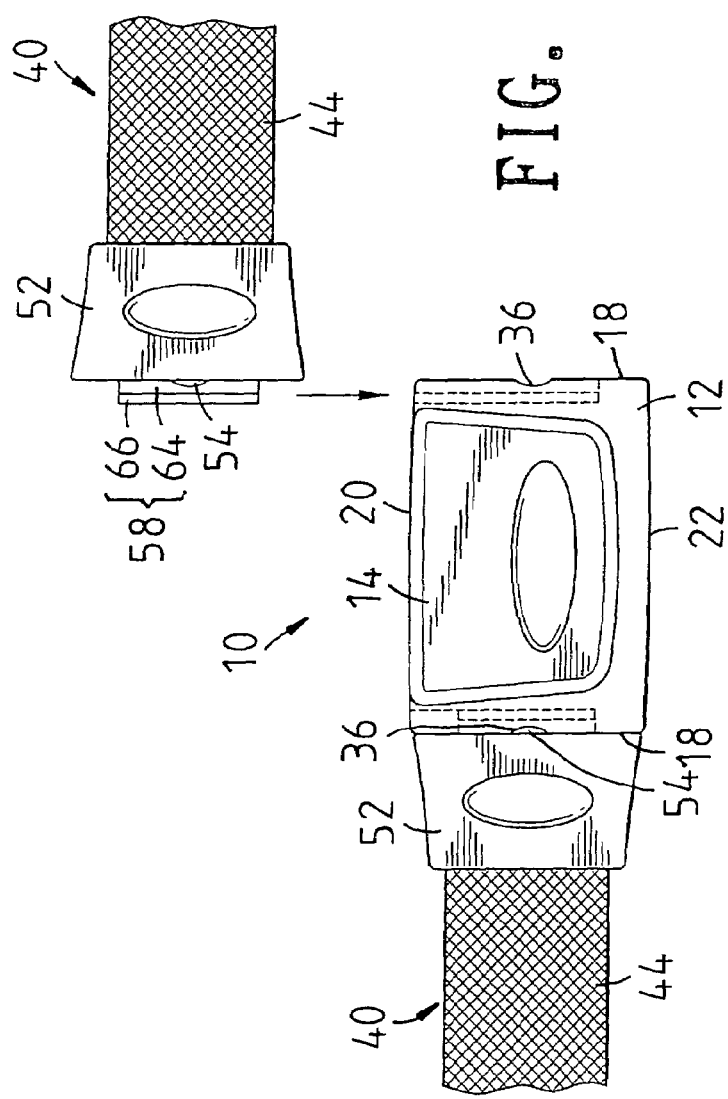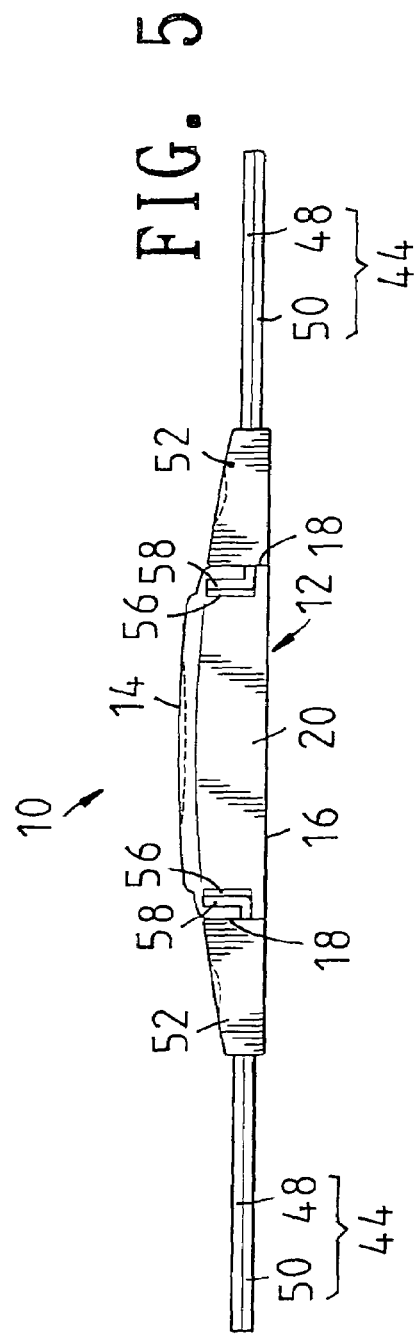

HEART RATE MONITOR ASSEMBLY

FIELD OF THE INVENTION

The present invention relates to a heart rate monitor assembly wherein the data processor and the connection device are separated from each other.

BACKGROUND OF THE INVENTION

A conventional heart rate monitor assembly generally includes a flexible belt, a measuring device and a display unit. The flexible belt is arranged to the user's chest and the measuring device is located at the position where the user's heart is located so as to detect the user's heartbeat. The measured information can be disclosed on the display unit. Usually, the measuring device is composed of a data processing unit and conductive plates, once either one of the data processing unit or the conductive plate needs to be replaced with a new one, the whole measuring device has to be discarded.

The present invention intends to provide a heart rate monitor assembly wherein the measuring device includes a date processor and two conductive plates and the belt has two connection ends which are easily connected to a case so as to be in contact with the conductive plates to provide electric power to the data processor.

SUMMARY OF THE INVENTION

The present invention relates to a heart rate monitor assembly which comprises a case in which a data processor and a power supply device are received therein. Two conductive plates are connected to the data processor and located in the case. A belt has two connection ends and each connection end has a connector which is removably connected to the conductive plate corresponding thereto.

The present invention will become more obvious from the following description when taken in connection with the accompanying drawings which show, for purposes of illustration only, a preferred embodiment in accordance with the present invention.

BRIEF DESCRIPTION OF THE DRAWINGS

FIG. 4 shows one of the connector is to be inserted into the L-shaped hole in the case, and FIG. 5 shows a top view of the case with the two connectors connected to the case.

DETAILED DESCRIPTION OF THE PREFERRED EMBODIMENT

Figure 1:
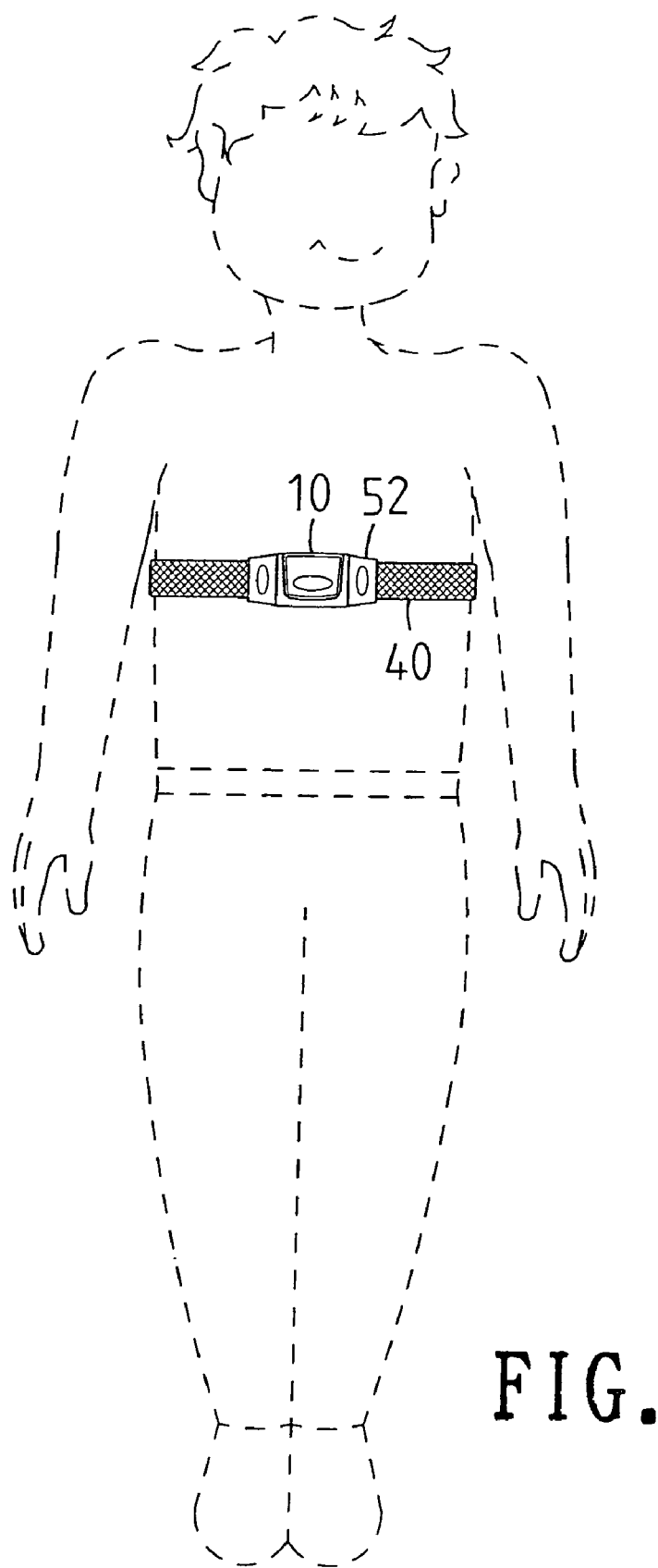
FIG. 1 show a user wears the heart rate monitor assembly of the present invention.
Figure 2:
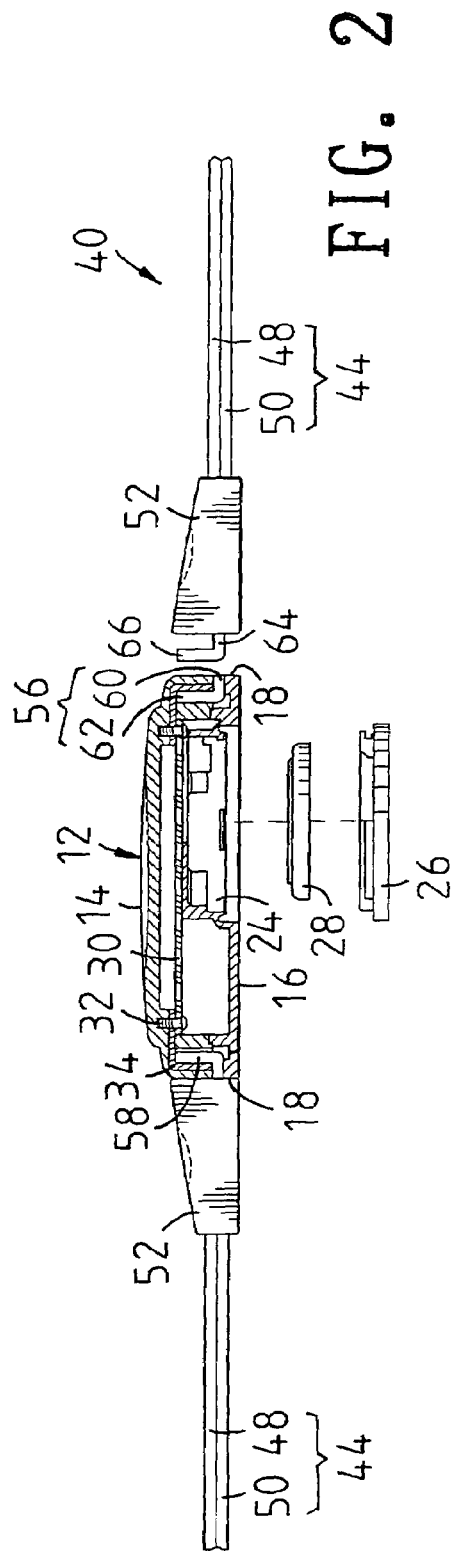
FIG. 2 is an exploded view to show the heart rate monitor assembly of the present invention.
Figure 3:
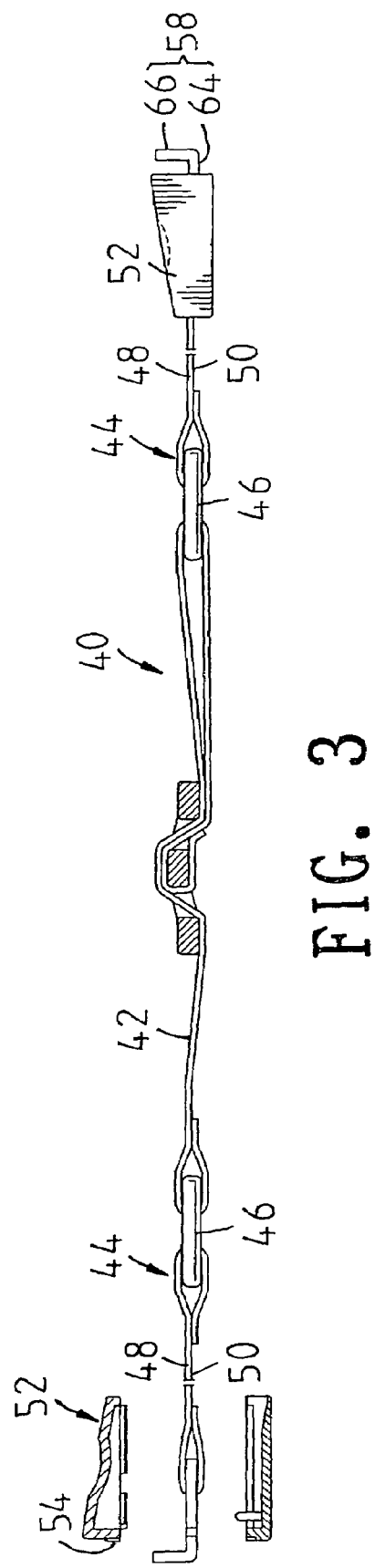
FIG. 3 shows the belt of the heart rate monitor assembly of the present invention.

Referring to FIGS. 1 to 5, the heart rate monitor assembly of the present invention comprises a data processing unit 10 and a belt 40. The data processing unit 10 includes a case 12 which includes a front 14, a rear side 16, two ends 18, a top surface 20 and a bottom 22. A chamber 24 is defined in the rear side 16 thereof and a processor 30 (a printed circuit board in this embodiment) is fixed to the case 12 and accessible from the chamber 24. A power supply device 28 (a battery in this embodiment) is also received in the chamber 24 and provides electrical power to the processor 30 and a cover 26 seals the chamber 24. The case 12 includes two L-shaped holes 56 defined in a top surface 20 and one of the two ends 18 thereof. Each L-shaped hole 56 is composed of a first hole 60 communicating with one of two ends 18 of the case 12 and a second hole 62 communicating with the top surface 20 of the case 12. Two conductive plates 34 each are an L-shaped plate which has a first end fixed to the data processor 30 by bolts 32 and the second end extends into the second hole 62 of the L-shaped hole 56 corresponding thereto. The second end of each conductive plate 34 is located at an inside of the second hole 62 and close to the end 18 of the case 12 as shown in FIG. 2.

The belt 40 includes an elastic section 42 and two connection ends 44 which are connected to two ends of the elastic section 42 by connection members 46. Each connection end 44 includes a conductive portion 50 and an outer layer 48. An end member 52 is connected on a distal end of each connection end 44 and each end member 52 has an L-shaped connector 58 extending therefrom. The L-shaped connector 58 is composed of a first section 64 and a second section 66. Each end member 52 includes a boss 54 extending from an end surface thereof and the case 12 includes two notches 36 defined in the two ends 18 thereof such that the two bosses 54 are engaged with the two notches 36 when the two connectors 52 are inserted into the two L-shaped holes 56 of the case 12.

When the connector 58 is inserted into the L-shaped hole 56 corresponding thereto, the first section 64 is engaged with the first hole 60, and the second section 66 is engaged with the second hole 62. The second sections 66 are in contact with the two respective second ends of the L-shaped conductive plates 34.

The user can easily wear the belt 40 on his/her body and the conductive portions 50 are in contact with the user's skin. When the two L-shaped connectors 58 are removably inserted into the two L-shaped holes 56 to be in contact with the conductive plates 34, the heartbeats or other physical conditions can be detected and are transferred to signals to the processor 30 which transfers the signals to a display unit which can be a wrist unit (not shown) to inform the user.

The case 12 and the connection ends 44 are separated so that they can be replaced individually. The width of the connectors 58 is equal or slightly smaller than the width of the case 12 so that the connection between the case 12 and the connectors 58 are reliable and strong. The elastic section 42 pulls the two connectors 58 in a direction away from the case 12 so that the second sections 66 can be firmly in contact with the second ends of the two conductive plates 34. The L-shaped connector 58 can be directly inserted into the L-shaped hole 56 without being flip over so that the users of any age can easily operate the assembly.

While we have shown and described the embodiment in accordance with the present invention, it should be clear to those skilled in the art that further embodiments may be made without departing from the scope of the present invention.

What is claimed is:

1. A heart rate monitor assembly comprising:
   a data processing unit having a case in which a data processor and a power supply device are received therein, the case including two L-shaped holes defined in a top surface and an end thereof;
   a belt having two connection ends and each connection end including a conductive portion and an outer layer, a connector connected to each of the connection ends, the conductive portion adapted to be in contact with a user's skin, and two conductive plates connected to the data processor and located in the two L-shaped holes, the connectors of the two connection ends being L-shaped connectors so as to be removably inserted into the two L-shaped holes to be in contact with the conductive plates.

2. The assembly as claimed in claim 1, wherein the case includes a chamber defined in a rear side thereof and the processor is accessible from the chamber, the power supply device is received in the chamber which is sealed by a cover.

3. The assembly as claimed in claim 1, wherein the belt has two end members .on two distal ends thereof and the two connectors respectively extend from the two end members, each end member includes a boss extending from an end surface thereof, the case includes two notches defined in the two ends thereof such that the two bosses are engaged with the two notches when the two connectors are inserted into the two L-shaped holes of the case.

4. The assembly as claimed in claim 1, wherein the two conductive plates each are an L-shaped plate which has a first end fixed to the data processor by bolts and a second end of each L-shaped conductive plate extends into the L-shaped hole corresponding thereto.

5. The assembly as claimed in claim 1, wherein each L-shaped hole is composed of a first hole communicating with one of the two ends of the case and a second hole communicating with the top surface of the case, the two conductive plates each are an L-shaped plate, which has a first end fixed to the data processor by bolts and a second end of each L-shaped conductive plate extends into the second hole of the L-shaped hole corresponding thereto, each of the L-shaped connectors is composed of a first section and a second section, the first section is engaged with the first hole and second section is engaged with the second hole, the second end of each conductive plate is located at an inside of the second hole and close to the end of the case so as to be in contact with the second section of the connector.

* * * * *